United States Patent
Ito

(10) Patent No.: US 6,817,977 B2
(45) Date of Patent: Nov. 16, 2004

(54) LIGHTING SYSTEM FOR AN ENDOSCOPE

(75) Inventor: Shunichi Ito, Tokyo (JP)

(73) Assignee: PENTAX Corporation, Tokyo (JP)

( * ) Notice: Subject to any disclaimer, the term of this patent is extended or adjusted under 35 U.S.C. 154(b) by 85 days.

(21) Appl. No.: 10/355,048

(22) Filed: Jan. 31, 2003

(65) Prior Publication Data

US 2003/0149340 A1 Aug. 7, 2003

(30) Foreign Application Priority Data

Feb. 5, 2002 (JP) .................................... 2002-027503

(51) Int. Cl.$^7$ .............................................. A61B 1/06
(52) U.S. Cl. .................... 600/180; 600/181; 362/574
(58) Field of Search ................................. 600/178, 180, 600/181; 362/574, 552

(56) References Cited

U.S. PATENT DOCUMENTS

| | | | |
|---|---|---|---|
| 4,322,129 A | | 3/1982 | Takahashi et al. |
| 4,425,599 A | * | 1/1984 | Rieder et al. ................ 362/552 |
| 5,006,965 A | * | 4/1991 | Jones .......................... 362/552 |
| 5,803,900 A | * | 9/1998 | Matsumoto et al. ......... 600/181 |
| 2001/0051763 A1 | | 12/2001 | Kurosawa et al. |

FOREIGN PATENT DOCUMENTS

| | | | |
|---|---|---|---|
| JP | 3-69277 | * | 3/1991 |
| JP | 10123434 | | 5/1998 |
| JP | 11119115 | | 4/1999 |
| JP | 1-340293 | | 12/2001 |

* cited by examiner

Primary Examiner—John P. Leubecker
(74) Attorney, Agent, or Firm—Greenblum & Bernstein, P.L.C.

(57) ABSTRACT

A lighting system for an endoscope includes a lamp positioned so that an optical axis thereof is oriented horizontally; a light guide having an incident end upon which the illuminating light from the lamp is incident; a diaphragm plate rotated about a pivot so as to advance into and retract from an optical path of the illuminating light, the pivot extending parallel to the optical axis of the lamp and positioned above or below the optical path. The diaphragm plate includes a notch which is formed at one end of the diaphragm plate, the notch being positioned along an arc which is centered about the pivot and which intersects a center of the light guide when the diaphragm plate rotates about the pivot; and a large number of minute perforations formed along and below the arc.

10 Claims, 4 Drawing Sheets

PRIOR ART

LIGHTING SYSTEM FOR AN ENDOSCOPE

BACKGROUND OF THE INVENTION

1. Field of the Invention

The present invention relates to a lighting system which supplies illuminating light to an end of a light guide for an endoscope.

2. Description of the Related Art

A xenon lamp, which is known as a high-intensity lamp with a low heating value, is widely used as a light source for inputting illuminating light to a light guide of an endoscope. In a state where the xenon lamp is fixed so that the axis thereof extends horizontally, the amount of light emitted from the xenon lamp oscillates in an area above the axial center of the light emitted from the xenon lamp due to the phenomenon of oscillation which occurs at convection or electrical discharge of the xenon gas sealed in the xenon lamp, or due to some other reason.

A small amount of such oscillations present no problem as long as the amount of the light having no fluctuations is relatively greater than that the amount of light having fluctuations when the degree of opening of a diaphragm is great. However, the fluctuations of the light amount show up as flicker in the illuminating light when the degree of opening of the diaphragm becomes small, and such flicker becomes more conspicuous as the degree of opening of the diaphragm decreases. This may obstruct the observing operation of the endoscope.

To prevent such a problem from occurring, there has been proposed a diaphragm device disclosed in Japanese Unexamined Patent Publication No.2001-340293. In this patent publication, as shown in FIG. 4, a pair of right and left diaphragm plates 91 are disposed to be capable of intercepting an optical path A of the illuminating light emitted from a lamp to the incident end of a light guide from the right and left sides of the optical path A, respectively. At least one of the pair of diaphragm plates 91 is provided with a projecting portion 92 which intercepts only an upper portion of the optical path A when the degree of opening of an aperture (i.e., the diaphragm plates 91) of the optical path A is extremely small.

The pair of diaphragm plates 91 are pivoted at a pivot 93 positioned straight above the optical path A. In a state where the degree of opening of an aperture of the optical path A is made extremely small by the pair of diaphragm plates 91, only a light bundle which is passed through a gap between the pair of diaphragm plates 91 which is formed in a vertically-lower half portion of the optical path A is incident on the incident end of a light guide.

In a conventional lighting device for an endoscope such as discussed above, the pair of diaphragm plates 91 must be rotated about the pivot 93 very finely to control the amount of illuminating light incident on the incident end of the light guide when the degree of opening of an aperture of the optical path A is extremely small.

Therefore, when a subject is observed closely through the endoscope, at the time the degree of opening of an aperture of the optical path A is generally made extremely small, even an extremely slight positional error or slight play in a drive system for driving the pair of diaphragm plates 91 tends to cause a substantial error in the amount of illuminating light incident on the incident end of the light guide, which makes the control of that amount of the incident light inaccurate.

Providing the drive system with reduction gearing having a high speed reduction ratio to prevent such a problem increases the number of elements of the drive system, and therefore increases the production cost of the drive system. At the same time, the amount of illuminating light incident on the incident end of the light guide cannot be controlled smoothly due to backlash and play occurring in such reduction gearing. As a result of this, a substantial delay (the extent to which is visually observable) occurs in control of the amount of illuminating light incident on the incident end of the light guide.

SUMMARY OF THE INVENTION

The present invention provides a lighting system for an endoscope which does not cause 'flicker' in the illuminating light incident on the incident end of a light guide due to the aforementioned phenomenon of oscillation that occurs at convection or electrical discharge of the xenon gas sealed in the xenon lamp, especially when the degree of opening of a diaphragm of the lighting system is extremely small, and which makes it possible to control the amount of illuminating light incident on the incident end of the light guide smoothly and precisely with a simple structure.

According to an aspect of the present invention, a lighting system for an endoscope is provided, including a lamp for supplying illuminating light, the lamp being positioned so that an optical axis thereof is oriented horizontally; a light guide having an incident end upon which the illuminating light from the lamp is incident; and a diaphragm plate rotated about a pivot so as to advance into and retract from an optical path of the illuminating light, the pivot extending parallel to the optical axis of the lamp and positioned one of above and below the optical path. The diaphragm plate includes a notch which is formed at one end of the diaphragm plate, the notch being positioned along an arc which is centered about the pivot and which intersects a center of the light guide when the diaphragm plate rotates about the pivot. A large number of minute perforations are formed along and below the arc.

It is desirable for the diameters of the large number of minute perforations to vary successively in a predetermined direction.

The large number of minute perforations can be aligned in a plurality of rows along the arc on the diaphragm plate.

The large number of minute perforations can be formed on the diaphragm plate at positions thereon no more than half of a radius of the optical path away from the arc.

It is desirable for the diameters of the large number of minute perforations to decrease in a direction away from the notch.

It is desirable for the diaphragm plate to rotate about the pivot so as to advance into and retract from the optical path in a direction orthogonal to the optical axis of the optical path.

It is desirable for the diaphragm plate to be fixed at one end thereof to a rotating shaft of a drive motor, the notch being formed at the other end of the diaphragm plate.

It is desirable for the pivot to extend parallel to the optical axis of the optical path.

Each perforation of the large number of minute perforations can be circular in shape.

It is desirable for the notch to be formed so as to be substantially symmetrical with respect to the arc, a width of the notch gradually decreasing in a direction along the arc toward an innermost portion of the notch.

The present disclosure relates to subject matter contained in Japanese Patent Application No.2002-27503 (filed on Feb. 5, 2002) which is expressly incorporated herein by reference in its entirety.

BRIEF DESCRIPTION OF THE DRAWINGS

The present invention will be described below in detail with reference to the accompanying drawings in which.

DESCRIPTION OF THE PREFERRED EMBODIMENT

Figure 2:
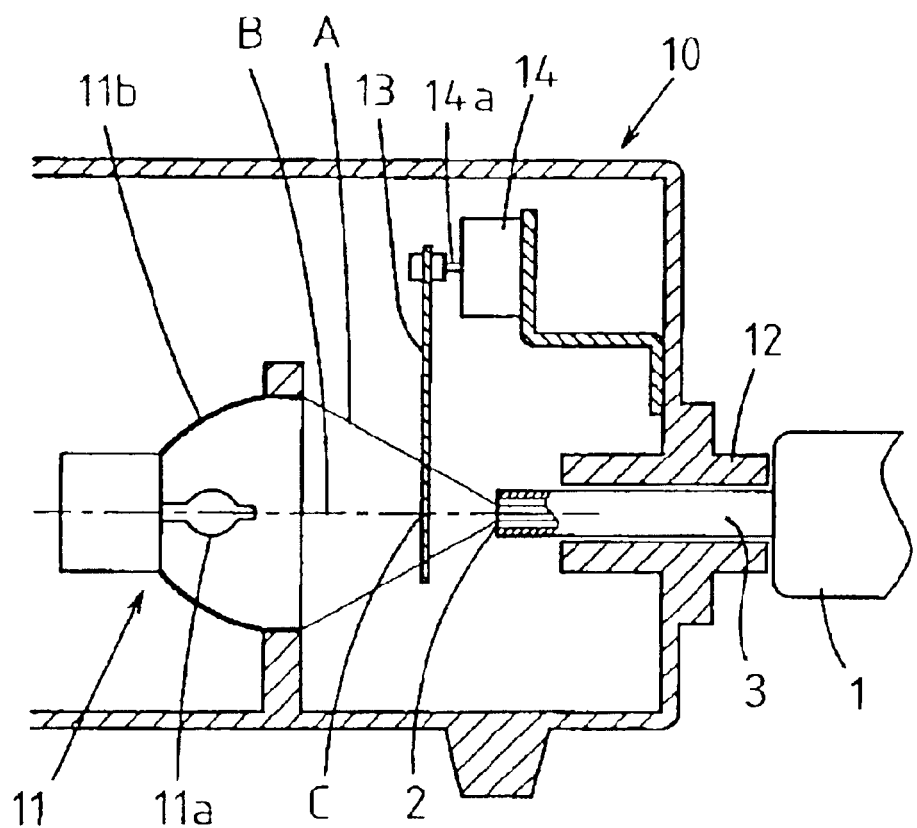
FIG. 2 is a cross sectional view of the lighting system shown in FIG. 1.

FIG. 2 shows a state where a light guide connector 1 for connecting a light guide 3 of an optical fiber endoscope (not shown) to a lighting system 10 is coupled to a connector socket 12 of the lighting system 10.

The lighting system 10 is provided therein with a lamp (light source) 11 which includes a xenon light bulb 11a and a concave reflector 11b. In the lamp 11, the xenon light bulb 11a is fixed so that the axis thereof extends horizontally while the concave reflector 11b is arranged so that the axis thereof is coincident with the axis of the xenon light bulb 11a to make the light reflected by the concave reflector 11b converge in the vicinity of an incident end 2 of the light guide 3.

The incident end 2 of the light guide 3 is positioned on an optical axis B of an optical path A of illuminating light emitted from the lamp 11 toward the incident end 2. The lighting system 10 is provided with a rotatable diaphragm plate (light intercepting plate) 13. The diaphragm plate 13 is disposed so that it can advance into and retract from the optical path A in a path between the lamp 11 and the incident end 2.

An upper end portion of the diaphragm plate 13 is fixed directly to a rotating shaft (pivot/pivotal shaft) 14a of a drive motor 14 which is positioned above the optical path A so that the diaphragm plate 13 can be driven to rotate about the rotating shaft 14a. The drive motor 14 can be, e.g., a servomotor.

The rotating shaft 14a of the drive motor 14 is arranged directly above the optical axis B to extend parallel to the optical axis B. Due to this arrangement, the diaphragm plate 13 can advance into and retract from the optical path A in a direction orthogonal to the optical axis B of the optical path A. Therefore, the degree of opening of an aperture of the optical path A depends on the rotational position of the diaphragm plate 13, and accordingly, the amount of illuminating light incident on the incident end 2 of the light guide 3 depends on the rotational position of the diaphragm plate 13.

Figure 1:
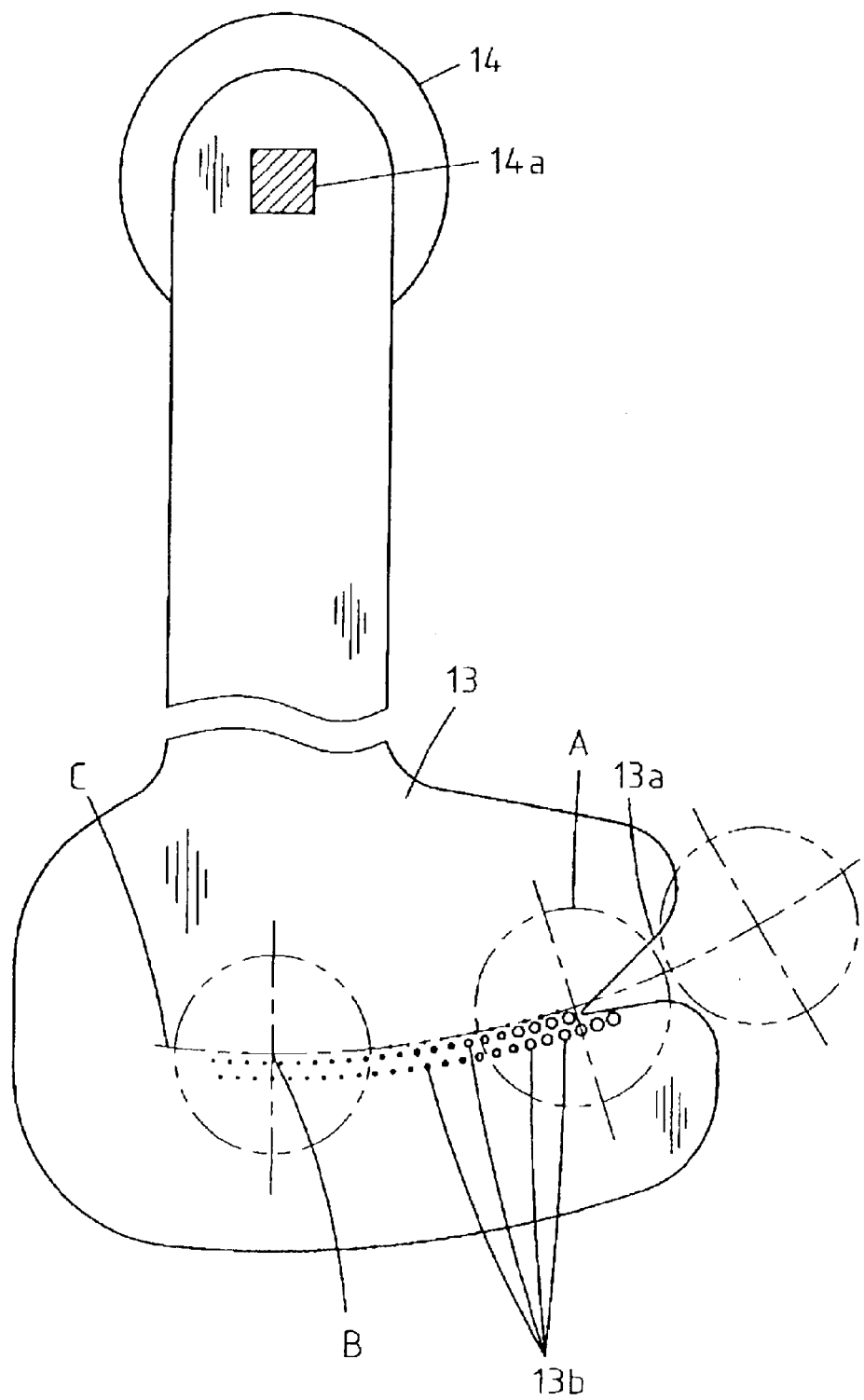
FIG. 1 is a front elevational view of a diaphragm plate of an embodiment of a lighting system for an endoscope, according to the present invention.

FIG. 1 shows a front elevational view of the diaphragm plate 13. The diaphragm plate 13 is formed as a substantially L-shaped plate as shown in FIG. 1, and is provided, at a free bottom end thereof on one side (right side as viewed in FIG. 1) of the free bottom end, with a notch 13a for varying the area of an aperture of the optical path A which is intercepted by the diaphragm plate 13 in accordance with the rotational position of the diaphragm plate 13.

A one-dot chain line arc C shown in FIG. 1 represents the moving path of the optical axis B which is generated on the diaphragm plate 13 when the diaphragm plate 13 rotates about the rotating shaft 14a relative to the optical axis B. The notch 13a is formed to be substantially symmetrical with respect to the arc C, and is further formed so that the width of the notch 13a gradually decreases in a direction toward the base (innermost portion) of the notch 13a.

Due to such a structure, when the degree of opening of an aperture of the optical path A is not extremely small, the area of an aperture of the optical path A which is intercepted by the diaphragm plate 13 varies by varying the position of the notch 13a with respect to the optical path A, which makes it possible to promptly control the amount of illuminating light incident on the incident end 2 of the light guide 3.

When a subject is observed closely through endoscope, the amount of illuminating light incident on the incident end 2 of the light guide 3 needs to be controlled finely in a state where the degree of opening of an aperture of the optical path A is extremely small.

To make such a fine control possible, the diaphragm plate 13 is provided thereon, along the arc C of the optical axis B of the optical path A, with a large number of circular minute perforations 13b.

The large number of minute perforations 13b are aligned in two rows and arranged at regular intervals in each row, and the diameters of the large number of minute perforations 13b decrease in a direction away from the notch 13a. With this structure, the area of an aperture of the optical path A which is intercepted by the diaphragm plate 13 varies by a variation of the rotational position of the diaphragm plate 13 in a state where the degree of opening of an aperture of the optical path A is extremely small.

Accordingly, the area of the aperture of the optical path A can be changed by a relatively large variation of the rotational position of the diaphragm plate 13. As a consequence, the amount of illuminating light incident on the incident end 2 of the light guide 3 can be finely controlled with the diaphragm plate 13 directly coupled to the rotating shaft 14a. Therefore, the amount of illuminating light incident on the incident end 2 of the light guide 3 can be controlled smoothly with no substantial delay and without being affected by any backlash or play like that which may occur if a reduction gear train or a cam mechanism was provided between the rotating shaft 14a and the diaphragm plate 13.

Figure 3:
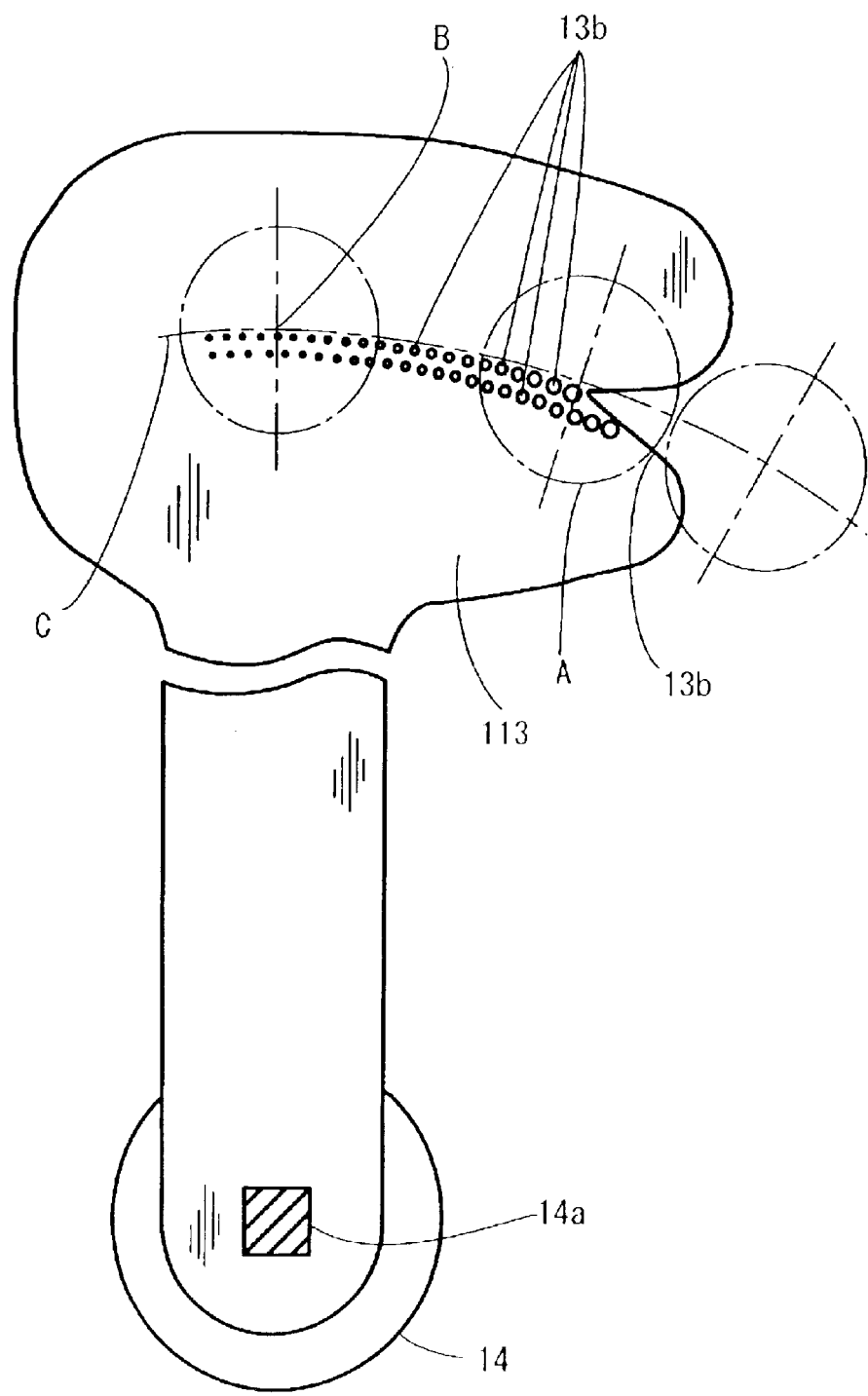
FIG. 3 is a front elevational view of a diaphragm plate of another embodiment of a lighting system for an endoscope, according to the present invention.
Figure 4:
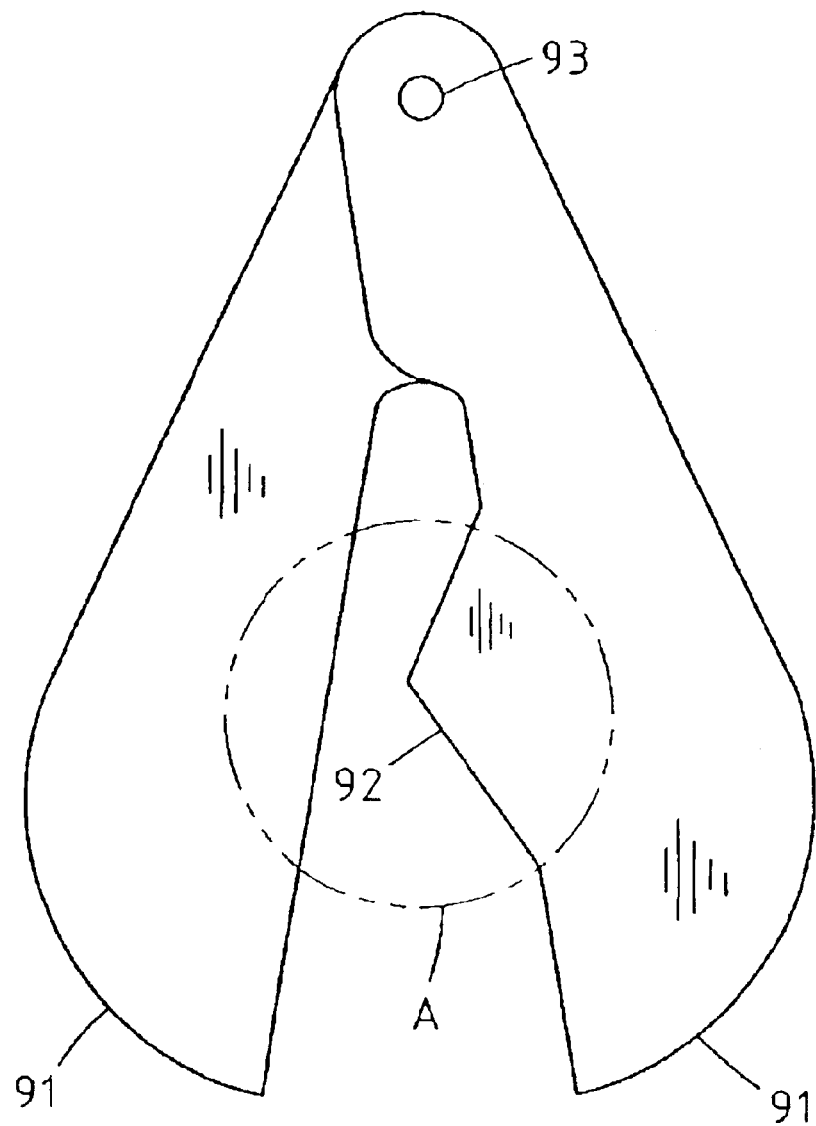
FIG. 4 is a front elevational view of a pair of diaphragm plates of a conventional lighting system.

In an alternative embodiment, as shown in FIG. 3, the rotating shaft 14a of the drive motor 14 is arranged directly below the optical axis B to extend parallel to the optical axis B. Due to this arrangement, similar to the embodiment shown in FIG. 1, a diaphragm plate 113 can advance into and retract from the optical path A in a direction orthogonal to the optical axis B of the optical path A In the illustrated embodiments shown in FIGS. 1 and 3, the large number of minute perforations 13b are formed on the diaphragm plate 13 below the arc C at positions no more than half of a radius of the optical path A away from the arc C. Due to this structure, only desirable light bundles in the vicinity of the optical axis B which are considered to exhibit a small range of variation in color temperature are incident on the incident end 2 of the light guide 3.

In addition, the large number of minute perforations 13b are formed on the diaphragm plate 13 along the arc C (i.e., a arc of the optical axis B which is generated on the diaphragm plate 13 when the diaphragm plate 13 is driven to rotate about the rotating shaft 14a of the drive motor 14) at positions only below the arc C.

Due to this structure, in a state where the degree of opening of an aperture of the optical path A is extremely small, all the light bundles emitted from an upper half of the xenon lamp bulb 11a, the light amount of which fluctuates, are intercepted by the diaphragm plate 13 to thereby prevent flicker from occurring in the illuminating light incident on the incident end 2 of the light guide 3.

Although the xenon lamp bulb 11a is used as a light source of the lamp 1 for inputting illuminating light to the light guide 3 in the above illustrated embodiment, the xenon lamp bulb 11a can be replaced by a different type of light source.

Although the large number of minute perforations 13b are formed on the diaphragm plate 13 at regular intervals in the above illustrated embodiment, a similar effect can be expected even if the large number of minute perforations 13b are formed at irregular intervals, and even if the minute perforations 13b are partly formed on the arc C.

As can be understood from the above description, according to a lighting system of an endoscope to which the present invention is applied, the amount of illuminating light incident on the incident surface of the light guide can be controlled by a relatively large rotation of the diaphragm plate since a large number of minute perforations for varying the area of an aperture of an optical path of the illuminating light in accordance with the rotational position of the diaphragm plate, in a state where the degree of opening of an aperture of the optical path of the of the illuminating light is extremely small, are formed on the diaphragm plate along a arc of the optical axis of the optical path which is generated on the diaphragm plate when the diaphragm plate rotates about a pivot. With this structure, the amount of illuminating light incident on the incident end of the light guide can be controlled smoothly and precisely with a simple structure especially when the degree of opening of an aperture of the optical path A is extremely small. Moreover, only desirable light bundles which do not generate any flicker in the illuminating light incident on the incident end of the light guide can be supplied to the incident end of the light guide since the large number of minute perforations are formed on the diaphragm plate 13 at positions thereon only below the arc on the diaphragm plate.

Obvious changes may be made in the specific embodiment of the present invention described herein, such modifications being within the spirit and scope of the invention claimed. It is indicated that all matter contained herein is illustrative and does not limit the scope of the present invention.

What is claimed is:

1. A lighting system for an endoscope, comprising:

a lamp for supplying illuminating light, said lamp being positioned so that an optical axis thereof is oriented horizontally;

a light guide having an incident end upon which said illuminating light from said lamp is incident; and a diaphragm plate rotated about a pivot so as to advance into and retract from an optical path of said illuminating light, said pivot extending parallel to said optical axis of said lamp and positioned one of above and below said optical path;

wherein said diaphragm plate comprises:

a notch which is formed at one end of said diaphragm plate, said notch being positioned along an arc which is centered about said pivot and which intersects a center of said light guide when said diaphragm plate rotates about said pivot, and a large number of minute perforations formed along and below said arc.

2. The lighting system for an endoscope according to claim 1, wherein diameters of said large number of minute perforations vary successively in a predetermined direction.

3. The lighting system for an endoscope according to claim 2, wherein said diameters of said large number of minute perforations decrease in a direction away from said notch.

4. The lighting system for an endoscope according to claim 1, wherein said large number of minute perforations are aligned in a plurality of rows along said arc on said diaphragm plate.

5. The lighting system for an endoscope according to claim 1, wherein said large number of minute perforations are formed on said diaphragm plate at positions thereon no more than half of a radius of said optical path away from said arc.

6. The lighting system for an endoscope according to claim 1, wherein said diaphragm plate rotates about said pivot so as to advance into and retract from said optical path in a direction orthogonal to said optical axis of said optical path.

7. The lighting system for an endoscope according to claim 1, wherein said diaphragm plate is fixed at one end thereof to a rotating shaft of a drive motor, said notch being formed at the other end of said diaphragm plate.

8. The lighting system for an endoscope according to claim 1, wherein said pivot extends parallel to said optical axis of said optical path.

9. The lighting system for an endoscope according to claim 1, wherein each perforation of said large number of minute perforations is circular in shape.

10. The lighting system for an endoscope according to claim 1, wherein said notch is formed to be substantially symmetrical with respect to said arc, a width of said notch gradually decreasing in a direction along said arc toward an innermost portion of said notch.

* * * * *